United States Patent [19]

Syrier

[11] 4,257,956
[45] Mar. 24, 1981

[54] OXABICYCLOALKANE PYRETHROID INTERMEDIATES

[75] Inventor: Johannes L. M. Syrier, Amsterdam, Netherlands

[73] Assignee: Shell Oil Company, Houston, Tex.

[21] Appl. No.: 135,405

[22] Filed: Mar. 31, 1980

[30] Foreign Application Priority Data

Apr. 6, 1979 [GB] United Kingdom ............... 12133/79

[51] Int. Cl.³ ........................................... C07D 493/04
[52] U.S. Cl. ......................... 260/343.21; 260/343.3 R
[58] Field of Search ..................................... 260/343.21

[56] References Cited

U.S. PATENT DOCUMENTS

| | | | |
|---|---|---|---|
| 3,071,600 | 1/1963 | Tinsley | 260/348.54 |
| 3,723,469 | 3/1973 | Martel | 260/343.3 R |
| 4,166,063 | 8/1979 | Martel et al. | 260/343.3 R |

OTHER PUBLICATIONS

Williamson et al., J. Org. Chem. 32, pp. 3934–3937, 1967.

*Primary Examiner*—Henry R. Jiles
*Assistant Examiner*—Jane T. Fan

[57] ABSTRACT

Oxidation of 3,7,7-trimethyl-5-oxo-4-oxabicyclo[4.1.0-]hept-2-ene with a peroxy acid affords the novel compound 2-acetoxy-6,6-dimethyl-4-oxo-3-oxabicyclo[3.1.0]hexane (IV) via the novel compounds 2,3-epoxy-3,7,7-trimethyl-5-oxo-4-oxabicyclo[4.1.0]heptane (II) and 2-acetyl-6,6-dimethyl-4-oxo-3-oxabicyclo[3.1.0-]hexane (III). The four compounds are intermediates to pyrethroid insecticides.

2 Claims, No Drawings

4,257,956

OXABICYCLOALKANE PYRETHROID INTERMEDIATES

BACKGROUND OF THE INVENTION

1. Field of the Invention

The present invention relates to new oxabicycloalkanes and to processes for their preparation. The compounds are useful materials in the preparation of insecticidally active synthetic pyrethroids.

2. Description of the Prior Art

The general formula of one class of pyrethroids described in U.S. Pat. No. 4,024,163 may be represented as follows:

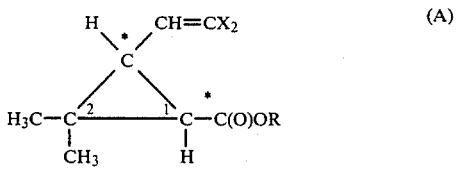

where each asterisk denotes an asymmetric carbon atom; each X is a halogen atom and R is a member of a group of radicals known to impart insecticidal activity to the molecule, e.g. 3-phenoxybenzyl or alpha-cyano-3-phenoxybenzyl. As these pyrethroids combine exceptionally good insecticidal properties with a very low mammalian toxicity, they are of great interest to the agrochemical industry and considerable effort has been expended in finding economic routes for their production.

It is known that the stereoisomeric form of the acid portion of the ester of formula A should be in the (1R, cis) form for maximum insecticidal activity, i.e. the absolute configuration at carbon atom 1 is R and the two hydrogen atoms on carbon atoms 1 and 3 are in a cis relationship. This nomenclature is known as the Elliott nomenclature and is defined in M. Elliott, A. W. Farnham, N. F. James, P. H. Needham and D. A. Pullman, Nature, 248, 710 (1974).

It follows, therefore, that if these stereoisomeric esters of formula A are to be prepared, either a stereospecific chemical route is required or the desired stereoisomer must be obtained from a racemic form by physical separation techniques. The latter are expensive and laborious and not readily employed on an industrial scale. In a stereo-specific route the naturally-occurring substance (+)-3-carene is used, whose formula is as follows:

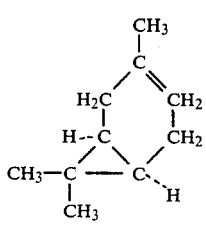

This compound is an inexpensive, readily available, natural terpene and in the present application are disclosed processes in a stereo-specific route from (+)-3-carene to pyrethroid esters of formula A.

SUMMARY OF THE INVENTION

The invention provides the compound 2-acetoxy-6,6-dimethyl-4-oxo-3-oxabicyclo[3.1.0]hexane per se. This compound—also referred to hereinafter as "compound IV"—has the following structural formula:

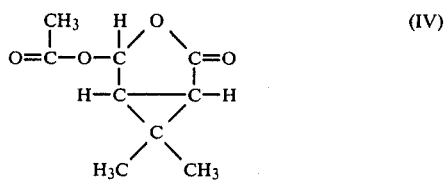

The invention also provides a process for the preparation of compound IV, which comprises the epoxidation of 3,7,7-trimethyl-5-oxo-4-oxabicyclo[4.1.0]hept-2-ene—also referred to hereinafter as "compound I'-'—with formation of 2,3-epoxy-3,7,7-trimethyl-5-oxo-4-oxabicyclo[4.1.0]heptane—hereinafter also referred to as "compound II"—, the isomerization of the latter compound in the presence of an acid into 2-acetyl-6,6-dimethyl-4-oxo-3-oxabicyclo[3.1.0]hexane—hereinafter also referred to as "compound III"—and the oxidation of the latter compound.

Compounds I, II and III have the following structural formulae:

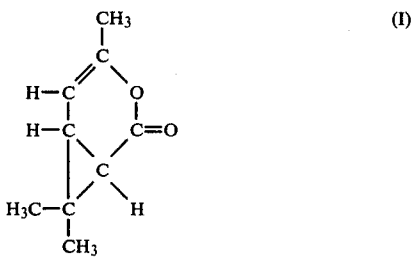

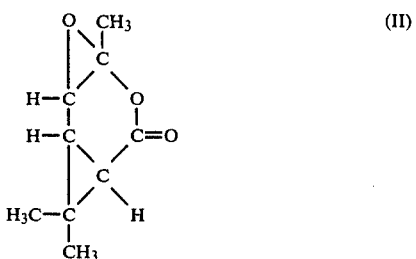

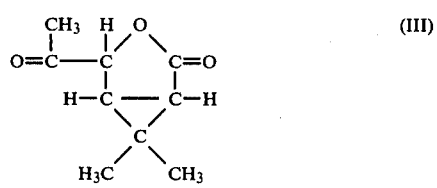

The starting material, compound I, is a known product of (+)-3-carene as illustrated in U.S. Pat. No. 4,132,717. Compound I may be prepared by dehydrating cis-2,2-dimethyl-3-(2-oxopropyl)cyclopropanecarboxylic acid with acetic anhydride in the presence of p-toluenesulfonic acid and a solvent, for example, toluene or benzene.

Compounds II and III are also novel and the invention provides these two compounds per se. Owing to the presence of two chiral carbon atoms in the cyclopropane ring, compounds II, III and IV exist in two optical isomers (ignoring the presence of the other chiral carbon atoms in the molecules), one having the 1R and the other the 1S configuration. The number 1 indicates the carbon atom of the cyclopropane ring bound to the group —O—C(O)—. The three compounds may consist of either the 1R or the 1S configuration or they may be a mixture of the two configurations. The 1R configuration of compounds II, III and IV is preferred.

The epoxidation of compound I may be carried out with any suitable epoxidation agent, for example, (a) a peroxy acid or (b) hydrogen peroxide in combination with a catalyst or (c) an alkyl hydroperoxide, for example, tert-butyl hydroperoxide, in combination with a catalyst. Peroxy acids are capable of rapidly and quantitatively converting compound I with a high selectivity to compound II.

The selectivity to a certain compound, expressed in a percentage, is defined as (a/b)×100 wherein "a" is the amount of the starting compound converted into that certain compound and "b" is the amount of converted starting compound.

Examples of suitable acids for the isomerization of compound II are alkanoic acids and traces of p-toluenesulfonic acid and of mineral acids. Alkanoic acids are usually capable of rapidly and quantitatively isomerizing compound II into compound III. Suitably, compound III is prepared by epoxidation of compound I with formation of compound II, followed by isomerization of compound II in the presence of an acid.

The epoxidation and isomerization referred to above may suitably be carried out at a temperature in the range of from, for example, 0° to 100° C.; an advantage is that these reactions usually proceed very well at a temperature in the range of from 10° to 40° C. Ambient temperature, for example, may be used. The epoxidation is suitably carried out at a molar ratio of peroxy acid to compound I in the range of from 1 to 2, but molar ratios higher than 2 are not precluded.

The invention also provides a process for the preparation of compound IV, which comprises the oxidation of compound III. This oxidation is a so-called Bayer-Villiger oxidation, as described in "Methoden der organischen Chemie" (Houben-Weyl), Volume VII/2B (1976), pp. 1984–1986, and is suitably carried out with a peroxy acid, thus giving a high yield of compound IV. Suitable temperatures are in the range of from 30° to 90° C.— temperatures outside this range are not precluded—and suitable molar ratios of peroxy acid to compound III are in the range of from 2 to 5, but molar ratios outside this range are not precluded. Examples of peroxy acids are persulfuric acid, peracetic acid, perphthalic acid, persuccinic acid and pernonanoic acid. Very good results have been obtained with optionally substituted perbenzoic acids, for example, with 3-chloroperbenzoic acid. The processes described above are suitably carried out in a solvent, for example, chloroform, dichloromethane, carbon tetrachloride, acetone, ethyl acetate or acetic acid. Very good results have been obtained with chloroform. Suitably, compound IV is prepared by isomerization of compound II in the presence of an acid with formation of compound III followed by oxidation of compound III.

According to a preferred embodiment of the present invention the epoxidation of compound I with formation of compound II, the isomerization of compound II into compound III and the oxidation of compound III to compound IV are carried out with the aid of a peroxy acid in one single step. This embodiment has the advantage of requiring only one agent for the epoxidation, isomerization and subsequent oxidation, which are all effected in one reaction zone, without isolation of the intermediate compounds II and III.

Compound IV can be saponified, for example, in the presence of water, methanol and an alkali metal hydroxide, with formation of an alkali metal salt of 2-formyl-3,3-dimethylcyclopropanecarboxylic acid. This acid is hereinafter also referred to as "compound V" and has the following structural formula:

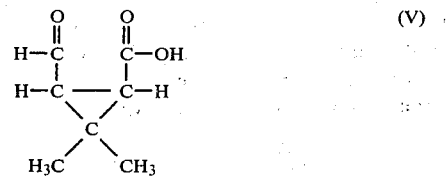

Compound (V) is a known compound and is converted into pyrethroid acids corresponding to the acid moiety in the formula (A) above by methods known in the art, for example, by forming the corresponding known alkyl ester of the above acid (V) and converting it to the pyrethroid acid of (A) using the two-step process described in European Pat. No. 2,849 or using the process described in the earlier mentioned U.S. Pat. No. 4,024,163.

EXAMPLES

The following Examples further illustrate the invention. Conversions and selectivities were determined by nuclear magnetic resonance (NMR) spectroscopy. The NMR data quoted were recorded at 90 MHz; the absorptions given are relative to a tetramethylsilane standard. Compounds I, II, III and IV all had the 1R configuration. Compound V had the 1R,cis configuration. The 3-chloroperbenzoic acid contained about 15% wt of 3-chlorobenzoic acid, calculated on 3-chloroperbenzoic acid.

PREPARATION OF COMPOUND I

The contents of a flask charged with 2,2-dimethyl-3-(2-oxo-propyl)cyclopropanecarboxylic acid (0.17 mol), p-toluenesulfonic acid monohydrate (0.016 mol), acetic anhydride (93 ml) and toluene (150 ml) were stirred for 30 minutes at a temperature between 10° and 20° C. The slightly darkened mixture was diluted with ether and washed with an ice cold saturated aqueous sodium hydrogen carbonate solution. The organic phase was dried over anhydrous magnesium sulfate and decolorized with charcoal. The solvent was evaporated at subatmospheric pressure to give a residue (24 g) of compound I. The yield of compound I was 93%.

EXAMPLE I—PREPARATION OF COMPOUND II

A 25 ml flask placed in a water bath having a temperature of 20° C. and provided with a magnetic stirrer was charged with compound I (6.4 mmol), 3-chloroperbenzoic acid (7.9 mmol) and chloroform (5 ml). After one hour's stirring compound I was quantitatively converted, with a selectivity to compound II of more than 90%. Then, dichloromethane (10 ml) and dimethyl sulphide (1 ml) were added and the resulting solution was washed with a saturated aqueous solution (10 ml) of sodium hydrogen carbonate and with two portions (each of 10 ml) of a 10%w aqueous solution of sodium chloride. The washed solution was dried over anhydrous magnesium sulfate and the volatile compounds were evaporated from the dried solution at sub-atmospheric pressure to leave an oily residue (1.1 g) of compound II.

The NMR spectrum of compound II showed the following absorptions in deuterochloroform:

$\delta = 1.30$ ppm, singlet, C$\underline{H}_3$—C—C$\underline{H}_3$
$\delta = 1.65$ ppm, singlet, C$\underline{H}_3$—C—O
$\delta = 1.6$ ppm, doublet, $\underline{H}$—C—C=O; J=8 Hz
$\delta = 1.33$ ppm, singlet, CH$_3$—C—C$\underline{H}_3$
$\delta = 2.05$ ppm, double doublet, $\underline{H}$—C—CH(—O—); J=2 Hz, 8 Hz
$\delta = 3.33$ ppm, doublet, $\underline{H}$—C—O; J=2 Hz

EXAMPLE II—PREPARATION OF COMPOUND II

An NMR tube placed in a water bath having a temperature of 20° C. was charged with compound I (0.5 mmol), 3-chloroperbenzoic acid (0.5 mmol) and deuterochloroform (1 ml). After 45 minutes' standing compound I was quantitatively converted; the sum of the selectivities to compounds II and III was 100% and the selectivity to compound II was more than 50%.

EXAMPLE III—PREPARATION OF COMPOUND III

After 3 hours' standing of the reaction mixture obtained in Example II, compound II was quantitatively converted into compound III. Then, dichloromethane (2 ml) and dimethyl sulphide (0.1 ml) were added and the resulting solution was first washed with a saturated aqueous solution (2 ml) of sodium hydrogen carbonate and then with two 2 ml portions of a 10%w aqueous solution of sodium chloride. The washed solution was dried over anhydrous magnesium sulfate and the volatile compounds were evaporated from the dried solution at sub-atmospheric pressure to leave a residue of compound III.

The NMR spectrum of compound III showed the following absorptions in deuterochloroform:

$\delta = 1.10$ ppm, singlet, C$\underline{H}_3$—C—C$\underline{H}_3$
$\delta = 1.6$ ppm, multiplet, $\underline{H}$—C—C(O)—O— $\delta = 2.31$ ppm, singlet, C$\underline{H}_3$—C=O
$\delta = 1.19$ ppm, singlet, CH$_3$—C—C$\underline{H}_3$
$\delta = 2.3$ ppm, multiplet, $\underline{H}$—C—CH(—O—)
$\delta = 4.90$ ppm, doublet, $\underline{H}$—C—O; J=6 Hz

EXAMPLE IV—PREPARATION OF COMPOUND IV

An NMR tube placed in a water bath having a temperature of 60° C. was charged with compound III (0.23 mmol, prepared as described in Example II), 3-chloroperbenzoic acid (0.35 mmol) and deuterochloroform (1 ml). After 24 hours' standing the conversion of compound III was 50%, with a selectivity to compound IV of more than 90%. Then, dichloromethane (2 ml) and dimethyl sulphide (0.1 ml) were added and the resulting solution was first washed with a saturated aqueous solution (1 ml) of sodium hydrogen carbonate and then with two 1 ml portions of a 10%w aqueous solution of sodium chloride. The washed solution was dried over anhydrous magnesium sulfate and the volatile compounds were evaporated from the dried solution at sub-atmospheric pressure to leave a residue of compound IV.

The NMR spectrum of compound IV showed the following absorptions in deuterochloroform:

$\delta = 1.20$ ppm, singlet, C$\underline{H}_3$
$\delta = 2.15$ ppm, singlet, C$\underline{H}_3$—C=O, multiplet for $\underline{H}$—C—C=O
$\delta = 1.44$ ppm, singlet, C$\underline{H}_3$—C—C$\underline{H}_3$
$\delta = 2.2$ ppm, multiplet, $\underline{H}$—C—C—O—C=O
$\delta = 6.63$ ppm, doublet, $\underline{H}$—C—O—C=O; J=5 Hz

EXAMPLE V—PREPARATION OF COMPOUND IV

An NMR tube placed in a water bath having a temperature of 20° C. was charged with compound I (0.60 mmol), 3-chloroperbenzoic acid (0.75 mmol) and chloroform (2 ml). After one hour's standing the tube contained 0.58 mmol of compound II. Then, another quantity of 3-chloroperbenzoic acid (0.84 mmol, dissolved in 1 ml of chloroform) was added and the temperature of the water bath was raised to 60° C. After 1 hour's standing compound II was quantitatively converted into compound III. Subsequently, two solutions of 3-chloroperbenzoic acid (0.50 mmol) in chloroform (1 ml) were added, one after a total of 20 hours and one 6 hours later. After a total of 30 hours' standing the conversion of compound III was 80%, with a selectivity to compound IV of 80 to 90%. Then, dichloromethane (2 ml) and dimethyl sulphide (0.3 ml) were added and the resulting solution was washed twice with a saturated aqueous solution (2 ml) of sodium hydrogen carbonate and with two portions (each of 2 ml) of a 10%w aqueous solution of sodium chloride. The washed solution was dried over anhydrous magnesium sulfate and the volatile compounds were evaporated from the dried solution at sub-atmospheric pressure to leave a residue containing compounds III and IV.

EXAMPLE VI—PREPARATION OF COMPOUND V

A 25 ml flask placed in a water bath having a temperature of 20° C. was charged with all of the residue obtained in Example IV, sodium hydroxide (0.4 mmol), water (1 ml) and methanol (1 ml). After 1.5 hours' standing water (2 ml) was added and the mixture obtained was washed with three portions (each of 2 ml) of dichloromethane. The washed aqueous liquid contained the sodium salt of compound V in a yield of more than 50%, calculated on starting compound I.

I claim:
1. 2,3-Epoxy-3,7,7-trimethyl-5-oxo-4-oxabicyclo[4.1.0]-heptane.
2. A compound of claim 1 which has the 1R configuration in which 1 refers to the carbon atom of the cyclopropane ring bound to the group —O—C(O)—.

* * * * *